United States Patent
Datta et al.

(10) Patent No.: US 7,452,990 B2
(45) Date of Patent: Nov. 18, 2008

(54) INTERMEDIATES FOR SYNTHESIS OF CEPHALOSPORINS AND PROCESS FOR PREPARATION OF SUCH INTERMEDIATES

(75) Inventors: Debashish Datta, Pune (IN); Muralikrishna Dantu, Pune (IN); Brijkishore Mishra, Pune (IN); Pollepeddi Lakshmi Narayana Sharma, Pune (IN)

(73) Assignee: Lupin Limited, Maharashtra (IN)

( * ) Notice: Subject to any disclaimer, the term of this patent is extended or adjusted under 35 U.S.C. 154(b) by 412 days.

(21) Appl. No.: 10/540,770

(22) PCT Filed: Dec. 26, 2002

(86) PCT No.: PCT/IN02/00245

§ 371 (c)(1),
(2), (4) Date: Dec. 2, 2005

(87) PCT Pub. No.: WO2004/058695

PCT Pub. Date: Jul. 15, 2004

(65) Prior Publication Data

US 2006/0135761 A1    Jun. 22, 2006

(51) Int. Cl.
C07D 501/22  (2006.01)
C07D 501/24  (2006.01)
C07D 501/36  (2006.01)
C07D 501/46  (2006.01)
C07D 501/34  (2006.01)
C07C 305/14  (2006.01)

(52) U.S. Cl. ............... 540/222; 540/225; 540/227; 540/228; 558/28

(58) Field of Classification Search ............. 558/28
See application file for complete search history.

(56) References Cited

U.S. PATENT DOCUMENTS

| | | | | |
|---|---|---|---|---|
| 5,037,988 A | * | 8/1991 | Diago Meseguer et al. . | 549/194 |
| 5,739,346 A | * | 4/1998 | Datta et al. ............ | 548/194 |
| 5,831,085 A | * | 11/1998 | Datta et al. ............ | 540/225 |
| 6,458,949 B1 | | 10/2002 | Handa et al. | |

FOREIGN PATENT DOCUMENTS

EP    0 791 597    8/1997

* cited by examiner

Primary Examiner—Mark L Berch
(74) Attorney, Agent, or Firm—Hamre, Schumann, Mueller & Larson, P.C.

(57) ABSTRACT

A novel 4-halo-2-oxyimino-3-oxo butyric acid-N,N-dimethyl formiminium chloride chlorosulfate of formula (I) useful in the preparation of cephalosporin antibiotics

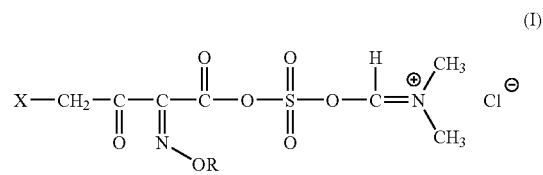

wherein X is chlorine or bromine; R is hydrogen, $C_{1-4}$ alkyl group, an easily removable hydroxyl protective group, $-CH_2COOR_5$, or $-C(CH_3)_2COOR_5$, wherein $R_5$ is hydrogen or an easily hydrolysable ester group. The compound of formula (I) is prepared by reacting 4-halo-2-oxyimino-3-oxobutyric acid of formula (IV¹),

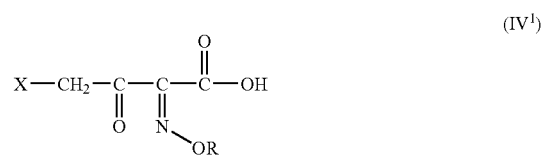

wherein X, R and $R_5$ are as defined above, with N,N-dimethylformiminium chloride chlorosulphate of formula (VII)

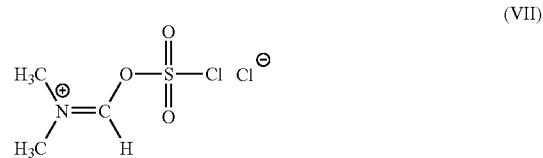

in an organic solvent at a temperature ranging from −30° C. to −15° C. The cephalosporins that may be prepared from the intermediate include cefdinir, cefditoren pivoxil, cefepime, cefetamet pivoxil, cefixime, cefmenoxime, cefodizime, cefoselis, cefotaxime, cefpirome, cefpodoxime proxetil, cefquinome, ceftazidime, cefteram pivoxil, ceftiofur, ceftizoxime, ceftriaxone and cefuzonam.

21 Claims, No Drawings

INTERMEDIATES FOR SYNTHESIS OF CEPHALOSPORINS AND PROCESS FOR PREPARATION OF SUCH INTERMEDIATES

FIELD OF THE INVENTION

The present invention relates to novel compounds of formula (I),

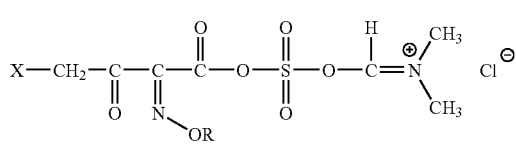

wherein X is chlorine or bromine; R is hydrogen, $C_{1-4}$ alkyl group, an easily removable hydroxyl protective group, $-CH_2COOR_5$, or $-C(CH_3)_2COOR_5$, wherein $R_5$ is hydrogen, or an easily hydrolysable ester group. The present invention also relates to a process for preparation of the compounds of formula (I). The invention also relates to the use of the novel compounds of formula (I) for preparation of cephalosporin antibiotics, in particular cephalosporin compounds of formula (II).

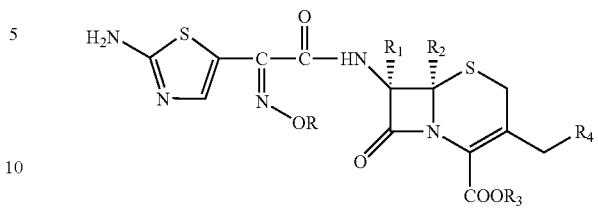

wherein R and $R_5$ are as defined above; $R_1$ is hydrogen or $-OCH_3$; $R_2$ is hydrogen; $R_3$ is hydrogen, a negative charge or together with the $COO^-$ group to which $R_3$ is attached is an ester, or an alkali or alkaline earth metal; $R_4$ is hydrogen or is a substituent useful in cephalosporin chemistry.

BACKGROUND OF THE INVENTION

Cephalosporin compounds of formula (II) are generally synthesised by two methods as described in the art. Both the methods involve amidification of the 7-amino function of the corresponding 3-(un)substituted cephalosporin derivative either directly with a 2-(2-amino thiazol-4-yl)-2-oxyimino acetic acid derivative (Method-I) or via Method-II a 4-halo-2-oxyimino-butyric acid derivative to give a 7-substituted cephalosporin addendum, which can be further elaborated to form the 2-(2-amino thiazol-4-yl)-2-oxyimino acetamido side chain and thereby, provide compounds of formula (II). The two methods of synthesis are summarized in Scheme-I.

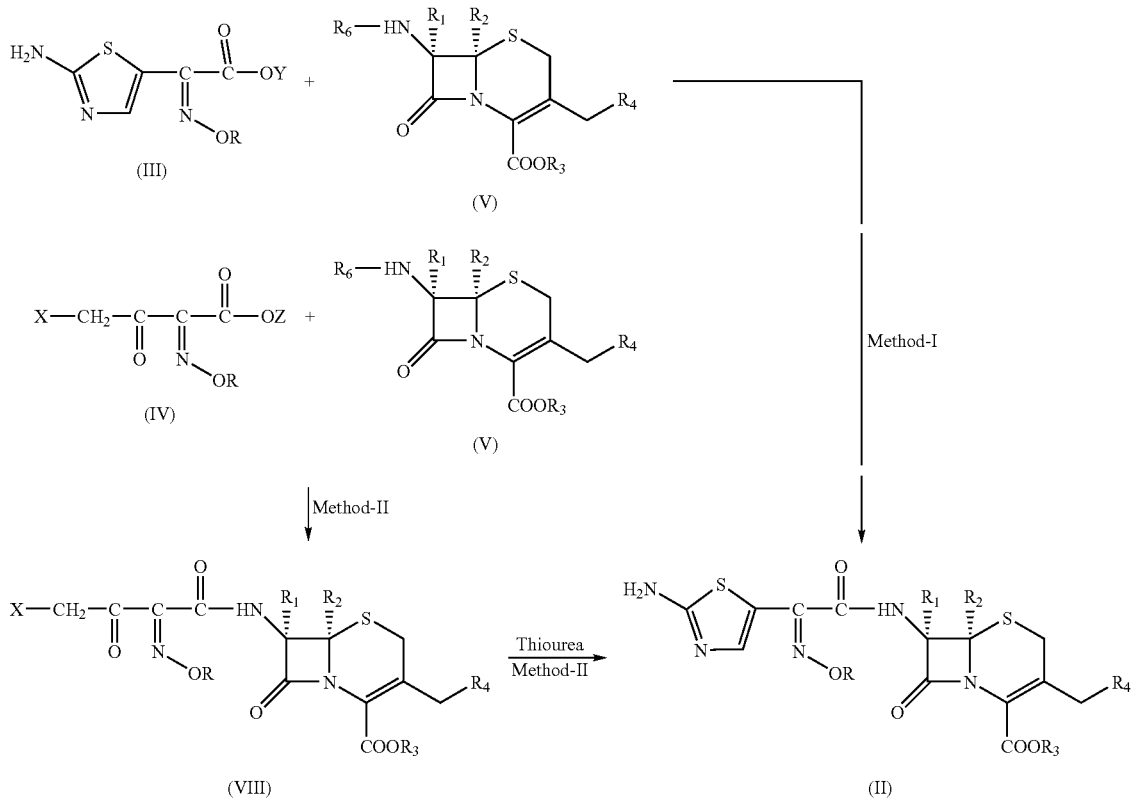

SCHEME-I: Prior Art methods for Synthesis of Compounds of Formula (II)

R is hydrogen, $C_{1-4}$ alkyl, ——$CH_2COOR_5$ or ——$C(CH_3)_2COOR_5$, $R_5$ is hydrogen, an easily hydrolysable ester group X is Cl or Br $R_1$ is hydrogen or $OCH_3$; $R_2$ is hydrogen; $R_3$ is hydrogen, a negative charge or together with the CO group to which $R_3$ is attached is an ester or an alkali or alkaline earth metal; $R_4$ is hydrogen or is a substituent useful in cephalosporin chemistry; $R_6$ is hydrogen or silyl In compounds of formula (III) of Method-I, the meanings of the groups X and R are as defined hereinearlier and the group Y is hydrogen or is a group which forms a basis that compound of formula (III) is in a reactive form. Similarly, in compound of formula (IV), of Method-II, the meanings of the groups X and R are as defined hereinearlier and the group Z is hydrogen or is a group which forms a basis that compound of formula (IV) is in a reactive form.

As per Method-I, synthesis of compound of formula (II) has been achieved by several ways, all differing in the choice of the reactive group Y. The following prior art methods illustrate the synthesis of compounds of formula (II) utilizing different reactive species as embodied in the group Y. These are to name a few;

i) U.S. Pat. No. 4,152,432 describes synthesis of cefotaxime comprising acylation of 7-aminocephalosporanic acid (7-ACA) with a compound of formula (III), wherein R is methyl and Y is a chlorine atom. In this method, the amino group of the thiazole ring is protected prior to amidification and subsequently deprotected by hydrolysis or hydrogenolysis.

Japanese Patent Nos. JP 52-102096, JP 53-157596 and British Patent No. GB 2 025 933 also utilize the same chemistry mentioned hereinbefore i. e. activation of the carboxylic acid as the acid halide. The acid halide, in particular the acid chloride is prepared by reaction of the 2-(2-amino thiazol-4-yl)-2-oxyimino acetic acid with $PCl_3$, $PCl_5$, $SOCl_2$ or $POCl_3$.

U.S. Pat. No. 3,954,745 also teaches a method for synthesis of cefazolin via the acid chloride method.

ii) Another method of activation of the carboxylic acid of formula (III), as disclosed in U.S. Pat. No. 5,317,099 is through formation of the activated ester by reaction of the carboxylic acid group with an acyloxyphosphonium chloride derivative. The method of preparation comprises reacting the carboxylic acid derivative (III) with triphenyl phosphine, hexachloroethane or carbon tetrachloride. However, this method increases the overall cost of the coupling reaction since it involves the use of expensive triphenyl phosphine.

iii) EP Patent Nos. EP 0 037 380 describes yet another method for synthesis of compounds of formula (II), specially cefotaxime and ceftriaxone, wherein the carboxylic acid group of compound (III) is activated as the benzothiazolyl thioester prior to formation of the amide bond at the 7-amino position. The benzothiazolyl thioester is turn prepared by reaction of the carboxylic acid compound (III) with bis[benzothiazolyl-(2)]disulfide and triphenyl phosphine, thereby rendering the method costly.

iv) U.S. Pat. No. 5,037,988 describes a process for production of compounds of formula (II), in particular, cefotaxime and ceftriaxone, in which the 2-(2-amino thiazol-4-yl)-2-oxyimino acetic acid (III) is activated as the dimethyl formiminium chloride chlorosulfite (DFCS) of formula (VI) and then coupled at the 7-amino position of the 3-substituted cephalosporin derivative to give compounds of formula (II).

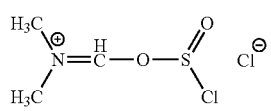
(VI)

The dimethyl formiminium chloride chlorosulfite (VI), is in turn prepared by reacting equimnolar quantities of thionyl chloride and N,N-dimethylformamide at room temperature. The method however, suffers from drawbacks inter alia in that the reaction can be effected in only specific solvents like benzene and toluene.

v) U.S. Pat. No. 5,739,346 describes a process for synthesis of β-lactam derivatives such as cefotaxime and ceftriaxone wherein compound (III) is activated as an adduct with N,N dimethyl formiminium chloride chlorosulfite (DFCCS) of formula (VII), prior to 7-amidification to give compounds of formula (II).

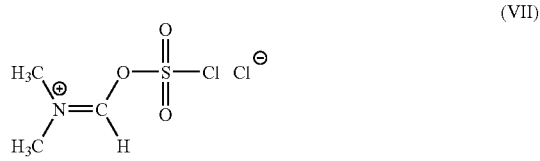
(VII)

vi) WO 99/51607 discloses a process for preparation of cefixime, wherein 7-amino-3-vinyl-3-cephem-4-carboxylic acid is reacted with compound (III) activated as the benzothiazolyl thioester.

vi) U.S. Pat. No. 6,388,070 provides yet another variation, wherein the compound (III) is activated as a 2-mercapto-5-substituted-1,3,4-oxadiazole derivative prior to 7-amidification to give compounds of formula (II).

The amidification has also been achieved by activation of the carboxylic acid (III) by formation of its mixed anhydride, an active amide or an active ester, as disclosed in U.S. Pat. No. 4,409,214; as the thiophosphoryl ester, as disclosed in U.S. Pat. No. 5,567,813 for synthesis of cefixime, cefotaxime, ceftriaxone, cefepime, cefpirome sulfate, ceftizoxime etc.

Synthesis of compounds of formula (II) as per Method-II is equally widely documented in the literature. Several methods, varying subtly in the choice of the reactive group Z of compounds of formula (IV) have been utilised, albeit the choice of the activating group is primarily restricted to acid halides. A few of such methods are disclosed in:

a) U.S. Pat. No. 4,559,334, discloses a method for synthesis of cefdinir, wherein the carboxylic acid (IV) activated as the acid chloride is reacted with 7-amino-3-vinyl-3-cephem-4-carboxylic acid to give the 7-substituted addendum, which on reaction with thiourea gives cefdinir.

b) U.S. Pat. No. 4,409,214 discloses a method identical for synthesis of cefixime, a structurally similar analogue of cefdinir.

c) U.S. Pat. No. 5,109,131 describes an advantageous process for preparation of cephalosporin compounds using tert-butyl-3-oxobutyrate as an intermediate. The tert-butyl-3-oxobutyrate is used for preparation of the compound (IV), which is reacted as such or a reactive derivative thereof is reacted with a 3-substituted-7-amino cephalosporin compound to form the 7-substituted cephalosporin addendum, which on reaction with thiourea gives compounds of formula (II).

The reactive derivatives utilised for 7-amidification as disclosed in U.S. Pat. No. 5,109,131 include acid halides, a mixed acid anhydride, an active amide or an active ester.

c) European Patent No. 0 030 294 discloses a method for preparation of ceftriaxone comprising reaction of 4-bromo-2-methoxyimino-3-oxobutyric acid chloride with 7-amino-3-desacetoxy-3-[2,5-dihydro-6-hydroxy-2-methyl-5-oxo-as-triazin-3-yl)-thio]-3-cephem-4-carboxylic acid to give the 7-amino addendum, which is cyclized with thiourea to give ceftriaxone.

d) European Patent No. 0 842 937 claims a process for preparation of cefotaxime and ceftriaxone comprising reaction of 7-ACA and 7-amino-3-desacetoxy-3-[2,5-dihydro-6-hydroxy-2-methyl-5-oxo-as-triazin-3-yl)-thio]-3-cephem-4-carboxylic acid respectively with 4-chloro-2-methoxyimino-3-oxobutyric acid, activated as 2-mercaptobenzothiazolyl ester, followed by cyclisation of the intermediates thus obtained with thiourea to give cefotaxime and ceftriaxone respectively.

e) U.S. Pat. No. 4,960,766 discloses a method for acylation at the 7-amino position of a 3-substituted cephalosporin derivative by reaction with compound (IV), which is activated as an acid halide or as a mixed anhydride, an activated amide or an activated ester in the presence of dicyclohexylcarbodiimide or an organic or inorganic base to give the corresponding acylated compound. Formation of the thiazolyl ring is completed when the acylated compound thus obtained is reacted with thiourea.

f) EP Patent No. 0 556 768 describes a method for preparation of ceftriaxone comprising reaction of 7-amino-3-desacetoxy-3-[2,5-dihydro-6-hydroxy-2-methyl-5-oxo-as-triazin-3-yl)-thio]-3-cephem-4-carboxylic acid with 4-chloro-2-methoxyimino-3-oxobutyric acid, activated as 2-mercaptobenzothiazolyl ester, followed by cyclisation of the intermediate thus obtained with thiourea to give ceftriaxone. This patent claims that the abovementioned reaction and subsequent conversion of ceftriaxone to its disodium hemiheptahydrate salt can be carried out in one pot using a mixture of acetone and water as solvent.

g) U.S. Pat. No. 6,384,215 provides yet another variation, wherein the compound (Iv) is activated as a 2-mercapto-5-substituted-1,3,4oxadiazole derivative prior to 7-amidification to give compounds of formula (II) after cyclisation of the intermediate compound with thiourea.

h) U.S. Pat. No. 6,458,949 discloses a process for preparation of ceftiofur by reacting silylated 7-amino-3-(2-furylcarbonylthiomethyl)-3-cephem-4-carboxylic acid with 4-bromo/chloro-2-methoxyimino-3-oxobutyryl acid halide, followed by cyclization of the compound thus formed with thiourea.

i) Published U.S. Patent Application No. 2002/0128469 A1 claims an improved method for preparation of compounds of formula (II), specially cefotaxime and ceftriaxone comprising reaction of compound (V, see Scheme-I) with compound (IV) activated as a reactive derivative to give the corresponding intermediate 7-acylated compound, the improvement being reaction of the intermediate 7-acylated compound thus obtained is cyclized with silylated thiourea to form the aminothiazole ring.

Surprisingly, the present inventors have found a novel manner of activation of the carboxylic acid of 4-halogeno-2-oxyimino-3-oxobutyric acid of formula (IV), which provides novel reactive derivatives of formula (I).

Thus, it is an object of the present invention to provide novel reactive derivatives of formula I.

Yet further object of the present invention is to provide a simple and cost-effective method for preparation of cephalosporin compounds of formula (II) utilising compounds of formula (I).

SUMMARY OF THE INVENTION

Thus the present invention according to one aspect provides novel compounds of formula (I)

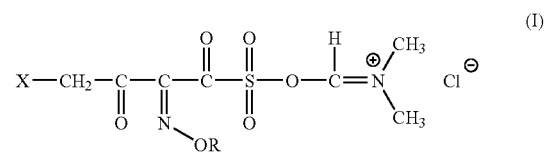

wherein X is chlorine or bromine;

R is hydrogen, $C_{1-4}$ alkyl group, an easily removable hydroxyl protective group, —$CH_2COOR_5$, or —$C(CH_3)_2COOR_5$, wherein $R_5$ is hydrogen, or an easily hydrolysable ester group.

According to another aspect of the present invention there is provided a method for preparation of compounds of formula (I) comprising reaction of 4-halo-2-oxyimino-3-oxobutyric acid of formula ($IV^1$),

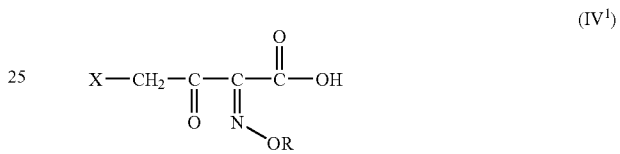

wherein X and R are as defined hereinbefore with N,N-dimethylformiminium chloride chlorosulphate of formula (VII)

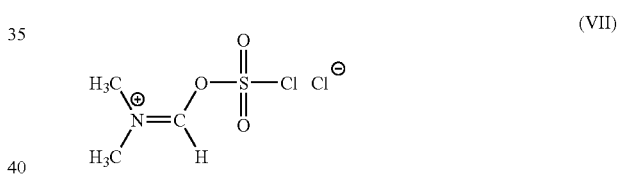

in an organic solvent at a temperature ranging from −30° C. to −15° C.

According to a further aspect of the present invention there is provided a process for preparation of cephalosporin compounds of formula (II)

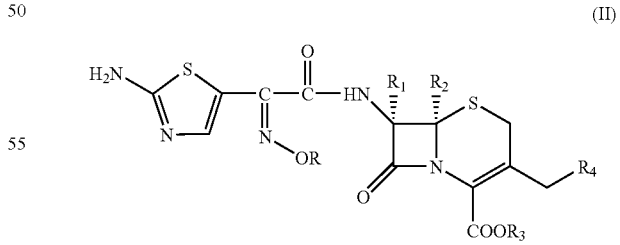

wherein R and $R_5$ are as defined above; $R_1$ is hydrogen or —$OCH_3$; $R_2$ is hydrogen; $R_3$ is hydrogen, a negative charge or together with the COO⁻ group to which $R_3$ is attached is an ester or an alkali or alkaline earth metal; $R_4$ is hydrogen or is a substituent useful in cephalosporin chemistry, the process comprising reaction of compound of formula (I)

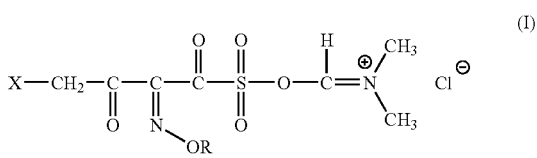

(I)

wherein X and R are as defined hereinbefore with 7-amino cephalosporanic acid of formula (V),

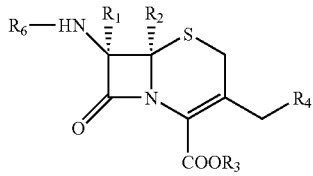

(V)

wherein $R_1$ is hydrogen or —$OCH_3$; $R_2$ is hydrogen; $R_3$ is hydrogen, a negative charge or together with the $COO^-$ group to which $R_3$ is attached is an ester, or an alkali or alkaline earth metal, or is a silyl group; $R_4$ is hydrogen or is a substituent useful in cephalosporin chemistry; and $R_6$ is hydrogen or a silyl group with the proviso that, when $R_3$ is hydrogen $R_6$ is also hydrogen; when $R_3$ is a silyl group $R_6$ is also a silyl group; and when $R_3$ is an ester, or an alkali or alkaline earth metal $R_6$ is hydrogen to give 7-[(4-halo-2-oxyimino-3-oxobutyramido-3-substituted-3-cephem-4-carboxylic acid of formula (VIII),

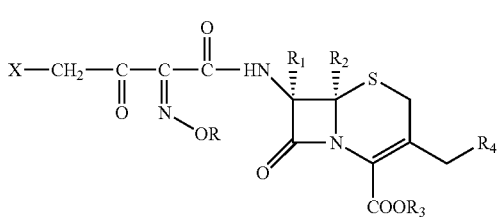

(VIII)

wherein X, R, $R_1$, $R_2$ and $R_4$ have the same meanings as defined hereinearlier and $R_3$ is hydrogen, a negative charge or together with the $COO^-$ group to which $R_3$ is attached is an ester, or an alkali or alkaline earth metal, followed by cyclisation of compound (VIII) with thiourea to give compounds of formula (II),

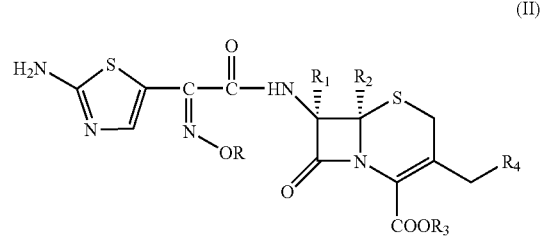

(II)

wherein R is hydrogen, $C_{1-4}$ alkyl group, an easily removable hydroxyl protective group, —$CH_2COOR_5$, or —$C(CH_3)_2COOR_5$, wherein $R_5$ is hydrogen, or an easily hydrolysable ester group; $R_1$ is hydrogen or —$OCH_3$; $R_2$ is hydrogen; $R_3$ is hydrogen, a negative charge or together with the $COO^-$ group to which $R_3$ is attached is an ester or an alkali or alkaline earth metal; and $R_4$ is hydrogen or is a substituent useful in cephalosporin chemistry.

The group $R_4$, which is a substituent useful in cephalosporin chemistry includes inter alia those substituents which are conventional in cephalosporin chemistry and which are useful in pharmaceutically active cephalosporins and thus include unsubstituted and substituted alkyl; unsubstituted and substituted alkenyl; alkyl and an alkenyl substituted by alkoxy, heterocyclthio, heterocycylcarbonylthio, alkylcarbonyloxy and heterocycyl. Heterocyryl includes 5 or 6 membered heterocycyl including a bicyclic ring system having 10 to 12 carbon atoms; a heterocycyl having 1 to 4 hetero atoms, selected from N, O or S.

DETAILED DESCRIPTION OF THE INVENTION

The process for the preparation of the compound of formula II the chemistry of which is summarized in reaction Scheme-II.

REACTION SCHEME-II: Method of Synthesis of Compounds (II) as per the Present Invention

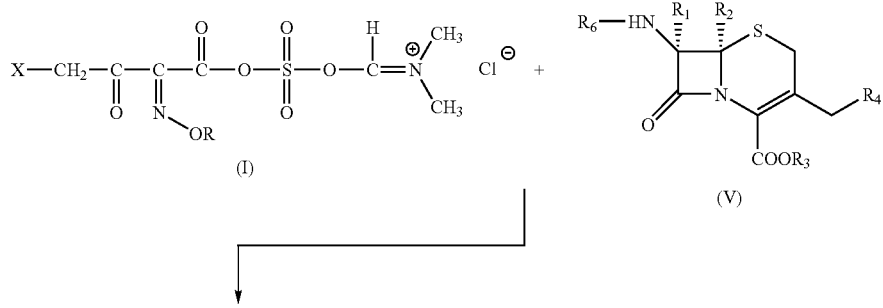

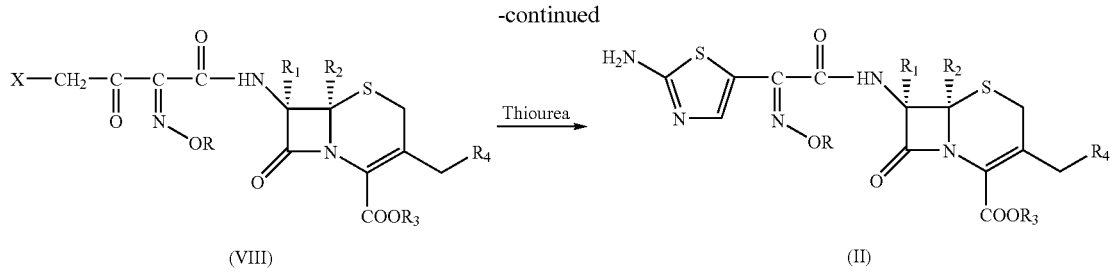

(VIII) → Thiourea → (II)

The abovementioned aspects of the present invention are illustrated hereinbelow in greater details.

1) Preparation of N,N Dimethyl Formiminium Chloride Chlorosulfite (DFCCS)(VII)

DFCCS (VII) is a known compound and described in the literature, viz. Z. Chem, 6 (4), 148 (1996); J.C.S. Perkin Trans I, 2004-2007 (1972); Bull Chem. Soc. Jpn., 58, 1063-1064; Adv Org Chem., 9 (2), 5, (1979); Synthetic Reagents, Vol. 4, 388-389; Angew Chem. Internal. Edit., 1 (12), 647 (1962); U.S. Pat. Nos. 5,739,346; 5,856,502; 5,945,532 and EP Patent No. 0 791 597.

While DFCCS (VII) prepared by any known process might be used, the inventors have found that best results are obtained when DFCCS (VII) is prepared by the following process.

The preferred process for obtaining the DFCCS (VII) comprises adding sulfuryl chloride to N,N-dimethylformamide at −20° C. The temperature is raised to 0° C. at which the solid adduct crystallized out, which is vigorously stirred at for one hour, followed by addition of dichloromethane to the resulting reaction mixture. The temperature was raised to 15° C. to 20° C. and at this temperature the solid crystals melt, resulting in the formation of an immiscible layer of the desired adduct, i. e. (VII).

Such mode of preparation of DFCCS (VII) is illustrated in Scheme III.

SCHEME-III: Method for preparation of DFCCS (VII)

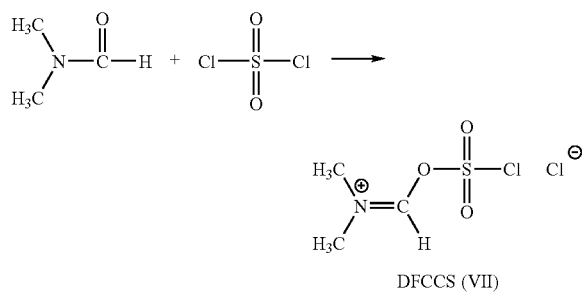

DFCCS (VII)

The DFCCS (VII) adduct thus obtained by the preferred process of the invention is found to be advantageous in use in the process of manufacture of the reactive derivatives of formula I in accordance with the objective of the invention for the reasons given below:

i) Unlike the complex, viz. dimethyl formiminium chloride chlorosulfite (DFCS) of formula (VI) utilized in the prior art, DFCCS (VII) used in the process of the present invention remains stable and does not get converted to the normal Vilsmeier's reagent. It has been observed that DFCCS (VII) of the present invention is apparently more stable than DFCS (VI), described in U.S. Pat. No. 5,037,988. In particular, it is found that the thus obtained DFCCS (VII) used in the process of the invention is distinct from thionly chloride-DMF adduct, i.e., dimethylformiminium chloride chlorosulfite (DFCS, VI) known in the art. The melting point of the latter is 138° C.-140° C. [Helv. Chim. Acta., 62, 1655 (1959)] while that of DFCCS (VII) is 40° C.-41° C. [Z. Chem., 6(4), 148 (1966)].

ii) The DFCCS (VII) used in the process of the invention can be prepared in any solvent such as benzene, toluene, acetonitrile or dichloromethane, and preferably, in the absence of solvents. This is advantageous and clearly distinct from the thionly chloride-DMF adduct, i.e., dimethyl formiminium chloride chlorosulfite (DFCS, VI) described in U.S. Pat. No. 5,037,988, which cannot be prepared in solvents such as chloroform or dichloromethane, since these solvents facilitate complete or partial conversion of dimethyl formiminium chloride chlorosulfite to normal Vilsmeier's reagent.

iii) It has been found that sulfuryl chloride-DMF adduct DFCCS of formula (VII) is more stable than DFCS (VI), made from thionly chloride and DMF. Thus, when DFCCS (VII) was kept at ambient temperature for 16 hours and used for further complexion with compounds of formula (V) for synthesis of the activated ester required for the final acylation reaction, the drop in yield for the final antibiotics was about 26% (85% when used fresh and 59% after storage of DFCCS for 16 hrs.). Similarly when DFCS adduct was kept at ambient temperature for 16 hrs. and further processed for synthesis of the final antibiotic, the drop in yield was about 35% (80% when used fresh and 45% when used after 16 hours). Hence, DFCCS obtained by the preferred process described above has superior stability compared to DFCS adduct of formula (VI).

Thus, the use of DFCCS (VII) for synthesis of the compound of formula (I), provides a practical, cost effective and safe method for manufacture of the desired cephalosporin antibiotics of formula (II).

2) Preparation of Novel Compounds of Formula (I):

The reactive compounds of formula (I) is prepared by the reaction of 4-halo-2-methoxy imino butyric acid (IV$^1$) and N,N-dimethyl formiminium chloride chlorosulfate i.e., DFCCS (VII) as obtained from Scheme-III.

In a typical reaction, DFCCS (VII) is added to 4-halo-2-oxyimino-3-oxo butyric acid (IV$^1$) in an organic solvent at a temperature of −25° C. to −15° C. and thereafter, the reaction mixture is stirred for two hours at a temperature of 5-10° C. The compound of formula (I) thus obtained can be stored at low temperature for a period of 3-6 hrs before use in the next step.

The process is summarized in Scheme-IV.

Any organic solvent can be used in the reaction for formation of compounds of formula (I). However, the formation of compound (I) is best prepared in chlorinated solvents selected from dichloromethane, dichloroethane, and chloroform; aromatic hydrocarbons selected from benzene and toluene; and nitrile solvents selected from acetonitrile, propionitrile and butyronitrile. However, chlorinated hydrocarbons are more preferred and among these dichloromethane is the preferred solvent.

The DFCCS (VII) is employed in molar to slightly more than molar proportions to the carboxylic acid compound (IV$^1$) used. Preferably, the molar ratio of the DFCCS (VII) to the carboxylic acid of formula (IV$^1$) is between 1.1 to 1.3.

SCHEME-IV: Method of preparation of Compounds of formula (I)

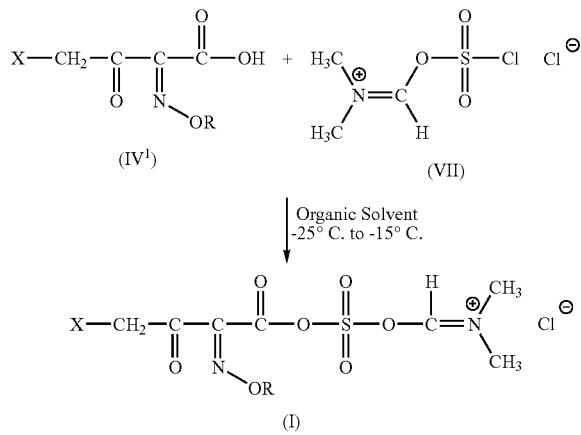

As mentioned hereinearlier, compounds of formula (I) obtained by the reaction summarized in Scheme-IV are relatively stable than other mixed anhydrides and the adduct of the carboxylic acid (IV$^1$) with DFCS of formula (VI) on storage at low temperatures. The novel compounds of formula (I) can be stored for a time period of 3-6 hours below −20° C.

The compounds of formula (I) exhibit distinct spectral properties as evidenced by their PMR, IR and Mass Spectra.

The PMR spectrum of the novel 4-bromo-2-methoxyimino-3-oxo butyric acid N,N dimethyl formiminium chloride chlorosulfite adduct of formula (I$^1$) was recorded neat with DMSo-d$_6$ as external lock at room temperature using CH$_2$Cl$_2$ as reference. The spectra shows two broad 1H signals at 13.4 ppm and 8.2 ppm respectively. Singlets due to —BrCH$_2$ and —OCH$_3$ are observed at 4.3 and 4.1 ppm respectively. The —N(CH$_3$)$_2$ signals appears at 3.2 and 3.1 ppm respectively.

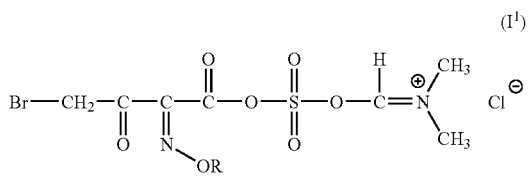

The IR spectrum of the freshly prepared bromo compound (I$^1$) shows signals at 1784 cm$^{-1}$ indicating anhydride functionality. After prolonged period of time, the signal disappears and a broad signal at 3379 cm$^{-1}$ appears, implying that the anhydride is unstable and gets hydrolysed to the acid.

The mass spectrum of the bromo compound (I$^1$) using a non-protic solvent at room temperature shows a signal of weak intensity at m/z 397.5 amu in the +APCI mode of ionization, indicative of the existence of the species of formula (I$^1$).

The PMR, IR and Mass Spectra of the bromo compound (I$^1$) are reproduced in FIG. 1, FIG. 2 and FIG. 3 respectively.

Of the chloro and bromo compounds of formula (I), the bromo compounds are preferred for use in synthesis of cephalosporin compounds of formula (II).

The carboxylic acid compounds of formula (IV$^1$) are known compounds and can be prepared in high purity and good yield starting from tert-butyl acetoacetate as described in U.S. Pat. Nos. 5,095,149 and 5,109,131.

3) Synthesis of Cephalosporin Compounds of Formula (II) Utilizing Novel Compounds of Formula (I).

The novel compounds of formula (I) are useful in the manufacture of valuable cephalsosporin antibiotics of formula (II), as per the method summarized in Scheme-II. The method provides a practical, cost-eefective and safe method for manufacture of the said cephalosporin antibiotics.

Compounds of formula (I) due to their inherent stability on storage are preferred over the other mixed anhydrides of the carboxylic acid (IV$^1$) or the adduct of the carboxylic acid (IV$^1$) with DFCS of formula (VI), which are somewhat less stable.

The process for manufacture of the desired cephalosporin antibiotics of formula (II) according the present invention basically involves the following steps, as summarized in Scheme-II.

SCHEME-II: Method of Synthesis of Compounds (II) as per the Present Invention

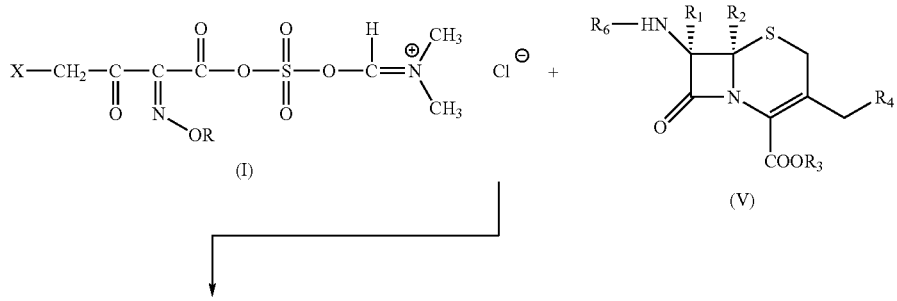

-continued

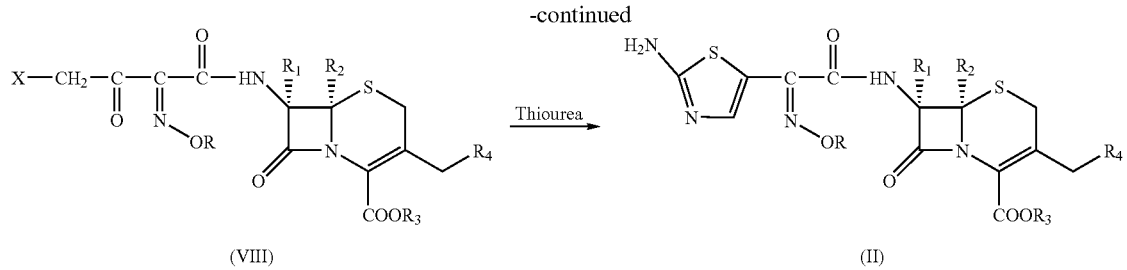

(VIII) (II)

A. Reaction of compound of formula (I) with the corresponding 7-amino-3-substituted cephalosporonic acid of formula (V) to give the 7-amino addendum of formula (VII), and
B. Reaction of the 7-amino addendum of formula (VIII) thus obtained with thiourea to give the cephalosporin antibiotics of formula (II).

In Step A of the process, the reactive compound (I) is treated with the 7-aminocephalosporanic acid of formula (V) in an organic solvent and in the presence of a base at a temperature ranging from −80° C. to −15° C., preferably −55° C. to −25° C. yield the 7-amino addendum of formula (VII).

In compounds of formula (V), $R_1$ is hydrogen or —$OCH_3$; $R_2$ is hydrogen; $R_3$ is hydrogen, a negative charge or together with the $COO^-$ group to which $R_3$ is attached is an ester, or an alkali or alkaline earth metal, or is a silyl group; and $R_4$ is hydrogen or is a substituent useful in cephalosporin chemistry; $R_6$ is hydrogen or a silyl group with the proviso that, when $R_3$ is hydrogen $R_6$ is also hydrogen; when $R_3$ is a silyl group $R_6$ is also a silyl group; and when $R_3$ is an ester, or an alkali or alkaline earth metal $R_6$ is hydrogen When $R_3$ is a negative charge, the group $R_4$ may contain a positive charge; e.g. in the form of a positively charged amine.

If $R_3$ together with the $COO^-$ group to which it is attached is an ester group $R_3$ preferably forms with the $COO^-$ group a physiologically hydrolysable and acceptable ester, e.g. $R_3$ is a substituent useful in cephalosporin chemistry.

By easily hydrolysable esters of the compounds of formula (II) it is to be understood compounds of the formula (II) in which the carboxyl group is present in the form of an ester group which can be easily hydrolysed. Examples of such esters, which can be of the conventional type, are the lower alkyl esters such as methyl, ethyl, tertiary butyl; alkanoyloxyalkyl esters, e.g. the acetoxy methyl, pivaloxymethyl, 1-acetoxyethyl, 1-pivaloxyethyl ester; the lower alkoxycarbonyloxyalkyl esters, e.g. the methoxycarbonyloxymethyl, 1-ethoxycarbonyloxyethyl and 1-isopropoxycarbonyloxyethyl ester; the alkoxymethyl esters, e.g. methoxy methyl ester, and the lower alkylaminomethyl esters, e.g. the acetamidomethyl esters. Other esters, e.g. the benzyl and cyanomethyl esters can also be used.

Alternatively, the compound of formula (V), in which $R_3$ and $R_6$ are hydrogen can be reacted with a silylating agent to effect silylation at the 4-carboxylic acid and the 7-amino position to form the corresponding (bis)-silylated compound of formula (V), wherein $R_3$ and $R_6$ are silyl groups, which is then reacted with the reactive compound (I) in an organic solvent and in the presence of a base at a temperature ranging from −80° C. to −15° C., preferably −55° C. to −25° C. to yield the 7-amino addendum of formula (VIII).

The silylation of compound (V) can be achieved by conventional ways using conventional silylating agents such as hexamethyldisilazane, trimethylchlorosilane, bis (trimethyl) silylacetamide etc. The silylated compound (V), thus obtained without isolation can be reacted with compounds of formula (I) to give the 7-amino addendum of formula (VIII).

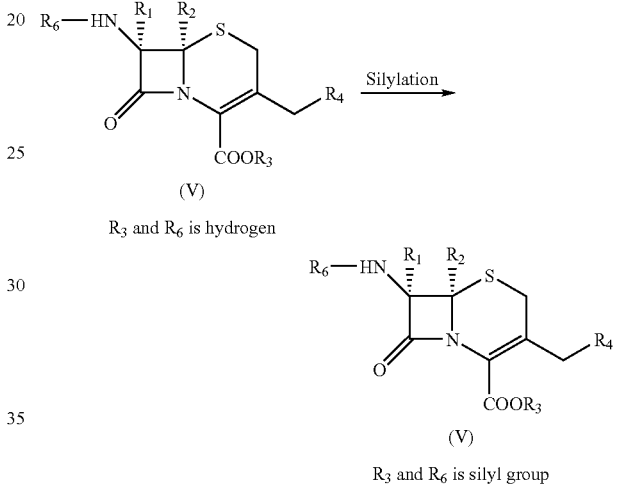

$R_3$ and $R_6$ is hydrogen $R_3$ and $R_6$ is silyl group

The basic compounds used as acid scavenging agent to capture HCl released during silylation include N,N dimethyl aniline, diethyl amine, pyridine, preferably N,N dimethyl aniline.

Any organic solvent can be used in the reaction for formation of compounds of formula (VIII). However, the formation of compound (VIII) is best carried out in chlorinated solvents selected from dichloromethane, dichloroethane, and chloroform; aromatic hydrocarbons selected from benzene and toluene; nitrile solvents selected from acetonitrile, propionitrile and butyronitrile; and ether solvents selected from tetrahydrofuran and dioxane. However, chlorinated hydrocarbons are more preferred and among these dichloromethane is the preferred solvent.

The compound (I) is employed in molar to slightly more than molar proportions to the cephalosporin compound (V) used. Preferably, the molar ratio of compound (I) to the cephalosporin compound (V) is between 1.1 to 2.0 and more preferably between 1.2 to 1.5.

Even though, both the non-silylated cephalosporin compound (V) or the silylated analogue can be used, because of the ease of reaction and the quality of the product obtained the silylated cephalosporin compound is the preferred one for reaction with compound (I) in forming the amide bond at the 7-position.

Compound (VIII) can be isolated from the reaction mixture by water and extraction of the product into a suitable organic solvent. The compound (VIII) can thereafter be isolated by evaporation of the solvent and optional crystallization of the residue thus obtained.

Alternatively, the compound of formula (VIII) need not be isolated and a solution of the same in an organic solvent can be used as such for reaction with thiourea to produce the cephalosporin antibiotics of formula (II).

In Step-B of the process, the compound of formula (II), either isolated or non-isolated, preferably the latter is reacted with thiourea in an organic solvent, optionally containing water and in the presence of a base at low to ambient temperature to effect formation of the aminothiazole ring and thereby, affording the cephalosporin antibiotic compounds of formula (II).

In a typical embodiment, a solution of the intermediate compound of formula (VIII) in a suitable organic solvent is treated with a solution of a mixture of thiourea and a base in water at low to ambient temperature for 2 to 3 hours at a pH between 5.0 to 6.0 to effect cyclisation of the aminothiazole ring and thereby, produce compounds of formula (II).

Any organic solvent can be used in the reaction for formation of compounds of formula (II). However, the formation of compound (II) is best carried out in chlorinated solvents selected from dichloromethane, dichloroethane, and chloroform; aromatic hydrocarbons selected from benzene and toluene; nitrile solvents selected from acetonitrile, propionitrile and butyronitrile; and ether solvents selected from tetrahydrofuran and dioxane. However, chlorinated hydrocarbons and ethers are more preferred and among these dichloromethane and tetrahydrofuran are the preferred solvents.

The base used in the reaction can be an organic or inorganic base, the latter being more preferred since it leads to minimum degradation of the cephalosporin ring. Alkali metal carbonate, such as sodium carbonate, potassium carbonate and lithium carbonate.; alkali metal hydrogen carbonates, such as sodium hydrogen carbonate and potassium carbonate; and alkali metal acetates, such as sodium acetate and potassium acetate can be used as bases.

The reaction is carried out at temperatures ranging from −5° C. to 40° C., preferably between −10° C. to 30° C.

At the end of the reaction the aqueous phase is separated from the organic phase and the compounds of formula (II) are isolated by standard methods known in cephalosporin chemistry.

In the cephalosporin antibiotic compounds of formula (II), R is hydrogen, $C_{1-4}$ alkyl group, an easily removable hydroxyl protective group,
—$CH_2COOR_5$, or —$C(CH_3)_2COOR_5$, wherein
$R_5$ is hydrogen, or an easily hydrolysable ester group;
$R_1$ is hydrogen or —$OCH_3$;
$R_2$ is hydrogen;
$R_3$ is hydrogen, a negative charge or together with the $COO^-$ group to which $R_3$ is attached is an ester or an alkali or alkaline earth metal;
$R_4$ is hydrogen or is a substituent useful in cephalosporin chemistry.

The group $R_4$, which is a substituent useful in cephalosporin chemistry includes inter alia those substituents which are conventional in cephalosporin chemistry and which are useful in pharmaceutically active cephalosporins and thus include unsubstituted and substituted alkyl; unsubstituted and substituted alkenyl; alkyl an alkenyl substituted by alkoxy, heterocyclthio, heterocycylcarbonylthio, alkylcarbonyloxy and heterocycyl. Heterocycyl includes 5 or 6 membered heterocycyl including a bicyclic ring system having 10 to 12 carbon atoms; a heterocycyl having 1 to 4 hetero atoms, selected from N, O or S;

When $R_3$ is a negative charge, the group $R_4$ may contain a positive charge; e.g. in the form of a positively charged amine.

If $R_3$ together with the $COO^-$ group to which it is attached is an ester group $R_3$ preferably forms with the $COO^-$ group a physiologically hydrolysable and acceptable ester, e.g. $R_3$ is a substituent useful in cephalosporin chemistry.

The term, "easily hydrolysable esters of the compounds of formula (II)" is to be understood as compounds of the formula (II) in which the carboxyl group to which the group $R_3$ or $R_5$ is attached is present in the form of an ester group which can be easily hydrolysed. Examples of such esters, which can be of the conventional type, are the lower alkyl esters such as methyl, ethyl, tertiary butyl; alkanoyloxyalkyl esters, e.g. the acetoxy methyl, pivaloxymethyl, 1-acetoxyethyl, 1-pivaloxyethyl ester; the lower alkoxycarbonyloxyalkyl esters, e.g. the methoxycarbonyloxymethyl, 1-ethoxycarbonyloxyethyl and 1-isopropoxycarbonyloxyethyl ester; the alkoxymethyl esters, e.g. methoxy methyl ester, and the lower alkylaminomethyl esters, e.g. the acetamidomethyl esters. Other esters, e.g. the benzyl and cyanomethyl esters can also be used.

The term, "an easily removable hydroxyl protective group" is to be understood as compounds of formula (II) in which the group R attached to the oxygen moiety of the oxyimino function are those which protect the oxygen function for further reaction with compound of formula (VII) during the preparation of compound of formula (I) and which can be conveniently be removed after formation of compounds of formula (I). Examples of such hydroxyl protective groups include those of the conventional types routinely used for protection of hydroxyl groups and include inter alia trialkyl silyl ethers; trialkylaryl silyl ethers; trialkyl stannyl ethers; trityl; tetrahydropyranyl; alkyl or aryl sulfonates such as tosyl, mesyl, besyl etc.; boron or aluminium containing two alkyl groups; (un)substituted benzyl etc.

Compounds of formula (II), wherein the group $R_3$ is hydrogen can be converted into their physiologically acceptable salts or esters by reaction of the carboxylic acid compound with suitable reagents that form the respective salts or esters. For instance, when compound of formula (II) is cefotaxime acid, ceftriaxone acid or ceftiofur acid it can be converted to the corresponding physiologically more active sodium salts by reaction with suitable sodium metal carriers. Similarly, when compound of formula (II) is cefpodoxime acid or cefditoren acid these can be converted into their respective physiologically more active esters like cefpodoxime proxetil and cefditoren pivoxil by reaction with the respective ester forming reagents.

Similarly, compounds of formula (II) in which the group R is an easily removable hydroxyl protective group can be converted to compounds of formula (II) in which R is hydrogen by removal of the protective groups by conventional means. For instance, cefdinir, in which the group R is hydrogen can be obtained by removal of any of the abovementioned hydroxyl groups.

Compounds of formula (II), wherein the group R attached to the oxime function is a group of $R_5$, such groups can be hydrolysed to a group, wherein R is hydrogen . For instance, cefixime and ceftazidime can be obtained by hydrolysis of the group $R_5$, which is tertiary butyl or the like in compounds of formula (II).

Alternatively, compounds of formula (II), wherein the group $R_3$ is an ester group can be converted to compounds wherein $R_3$ is hydrogen by removal of the ester function.

Further, the compounds of formula (II) may also be obtained as physiologically active solvates or hydrates.

It is to be understood all the abovementioned variations of the process form an embodiment of the present invention.

The commercially valuable cephalosporin compounds of formula (II) that can be manufactured by the process of this invention include, to name a few:

1) 7-[(Z)-2-(2-amninothiazol-4-yl)-2-hydroxyiminoacetamido]-3-vinyl-3-cephem-4-carboxylic acid i.e. cefdinir,
2) 7-[(Z)-2-(2-amino-4-thiazolyl)-2-methoxyimino)acetyl] amino-3-[(1Z)-2-(4-methyl-5-thiazolyl)ethenyl-3-cephem-4-carboxylic acid, i.e. cefditoren and the pivaloyloxymethyl ester i. e. cefditoren pivoxil,
3) 7-[(Z)-2-(2-aminothiazol-4-yl)-2-methoxyiminoacetamido]-3-(1-methylpyrrolodino)methyl-3-cephem-4-carboxylate i.e. cefepime,
4) 7-[(Z)-2-(2-aminothiazol-4-yl)methoxyiminoacetamido]-3-methyl-3-cephem-4-carboxylic acid i.e. cefetamet, and the pivaloyloxymethyl ester i. e. cefetamet pivoxil,
5) 7-[(Z)-2-(2-aminothiazol-4-yl)-2-carboxymethoxyiminoacetamido]-3-vinyl-3-cephem-4-carboxylic acid i.e. cefixime,
6) 7-[(Z)-2-(2-aminothiazol-4-yl)-2-methoxyiminoacetamido]-3-[[1-methyl-1H-tetrazol-5-yl]thio]methyl]-3-cephem-4-carboxylic acid i.e. cefmenoxime,
7) 7-[(Z)-2-(2-aminothiazol-4-yl)-2-methoxyiminoacetamido]-3-[[[5-carboxymethyl)-4-methyl-2-thiazolyl]thio] methyl]-3-cephem-4-carboxylic acid i.e. cefodizime,
8) 7-[(Z)-2-(2-aminothiazol-4-yl)-2-methoxyiminoacetamido]-3-[[2,3-dihydro-2-(2-hydroxyethyl)-3-imino-1H-pyrazol-1-yl]methyl]-3-cephem-4-carboxylic acid i.e. cefoselis,
9) 7-[(Z)-2-(2-aminothiazol-4-yl)-2-methoxyiminoacetamido]cephalosporanic acid i.e. cefotaxime,
10) 7-[(Z)-2-(2-aminothiazol-4-yl)-2-methoxyiminoacetamido]-3-[92,3-cyclopenteno-1-pyridinium)methyl]-3-cephem-4-carboxylic acid i.e. cefpirome,
11) 7-[(Z)-2-(2-aminothiazol-4-yl)-2-methoxyiminoacetamido]-3-methoxymethyl-3-cephem-4-carboxylate—i.e. cefpodoxime and the 1-methylethoxycarbonyloxy ether i. e. cefpodoxime proxetil,
12) 7-[(Z)-2-(2-aminothiazol-4-yl)-2-methoxyiminoacetamido]-3-[[1-azabicyclo[4.2.0]oct-2-en-3-yl]methyl-5,6,7-tetrahydroquinolinium-4-carboxylic acid inner salt i. e. cefquinome,
13) 7-[(Z)-2-(2-aminothiazol-4-yl)-2-(1-carboxy-1-methylethyl)oximinoacetamido}-3-[pyridinium]methyl-3-cephem-4-carboxylacid acid inner salt i. e. ceftazidime,
14) 7-[(Z)-2-(2-aminothiazol-4-yl)-2-methoxyiminoacetamido]-3-[2-(5-methyl-1,2,3,4-tetrazoyl)-methyl-3-cephem-4-carboxylic acid i. e. cefteram and the and the pivaloyloxymethyl ester i. e. cefteram pivoxil,
15) 7-[(Z)-2-(2-aminothiazol-4-yl)-2-methoxyiminoacetamido]-3-[[(2-furanylcarbonyl)thio]methyl]-3-cephem-4-carboxylic acid i. e. ceftiofur,
16) 7-[(Z)-2-(2-aminothiazol-4-yl)-2-methoxyiminoacetamido]-3-cephem-4-carboxylic acid i. e. ceftizoxime,
17) 7-[(Z)-2-(2-aminothiazol-4-yl)-2-methoxyiminoacetamido]-3-[[2,5-dihydro-6-hydroxy-2-methyl-5-oxo-as-triazin-3-yl)thio]methyl]-3-cephem-4-carboxylic acid i. e. ceftriaxone, and
18) 7-[(Z)-2-(2-aminothiazol-4-yl)-2-methoxyiminoacetamido]-3-[(1,2,3-thiadiazol-5-ylthio)methyl]-3-cephem-4-carboxylic acid i. e. cefuzonam.

The invention can be further illustrated by the following examples, which should not be construed as limiting the scope and spirit of the invention.

EXAMPLE-1

General method for Preparation of 4-halo-2-oxyimino-3-oxo butyric acid-N,N-dimethyl formiminium chloride chlorosulfate of formula (I)

N,N-dimethyl formamide (1.0 mole) is added to a mixture of sulfuryl chloride (1 mole) and of methylene chloride slowly over 30 mins, at a temperature of −20 to −10° C. The mixture is stirred for 2 hrs at 20-22° C. Further methylene chloride is added and the mixture is allowed to settle down. N,N-dimethyl formiminium chloride chlorosulfate (DFCCS, VII) that remains in the denser organic layer is separated.

The solution of DFCCS (VII) in methylene chloride is added to a solution of containing 0.75 moles of 4-halo-2-oxyimino-3-oxo-butyric acid of formula (IV$^1$) in methylene chloride over 30 min at −25 to −15° C. The reaction mixture was stirred for two hours at 5-10° C. to give the title compound (I). i. e. 4-halo-2-oxyimino-3-oxo butyric acid-N,N-dimethyl formiminium chloride chlorosulfate of formula (I)

EXAMPLE-2

Preparation of 4-bromo-2(Z)-methoxyimino-3-oxo butyric acid-N,N-dimethyl formiminium chloride chlorosulfate of formula (I)

26.6 g (0.364 moles) of dimethyl formamide was added to a mixture of 49.12 g (0.363 moles) of sulfuryl chloride and 50 ml of methylene chloride slowly over 30 mins, at a temperature of −20 to −10° C. The mixture was stirred for 2 hrs at 20-22° C. Further 200 ml of methylene chloride was added and the mixture was allowed to settle down. N,N-dimethyl formiminium chloride chlorosulfate (DFCCS, VII) that remains in the denser organic layer was separated.

The solution of DFCCS (VII) in methylene chloride was added to a solution of 63.39 g (0.283 moles) of 4-bromo-2 (Z)-methoxyimino-3-oxo-butyric acid (IV$^1$) in 800 ml of methylene chloride over 30 min at −25 to −15° C. The reaction mixture was stirred for two hours at 5-10° C. to give the title compound (I) i. e. 4-bromo-2-methoxyimino-3-oxo butyric acid-N,N-dimethyl formiminium chloride chlorosulfate of formula (I)

$^1$HNMR (DMSO-d$_6$): δ, 13.4 (s, 1H), 8.2 (s, 1H), 4.3 (s, —BrCH$_2$), 4.1 (s, —OCH$_3$), 3.2 and 3.1 (—N(CH$_3$)$_2$.

IR (main bands) in cm$^{-1}$: 1784

Mass Spectrum: m/z 397.5 amu in the +APCI ionization mode.

EXAMPLE-3

Preparation of Sodium salt of 7-[(Z)-2-(2-aminothiazol-4-yl)-2-methoxyiminoacetamido]cephalosporanic acid (cefotaxime sodium)

Step A: Preparation of 4-bromo-2-methoxyimino-3-oxo butyric acid-N,N-dimethyl formiminium chloride chlorosulfate of formula (I)

The title compound was prepared as described in Example-2.

Step B: Preparation of silylated 7-amino cephalosporanic acid:

81.0 g (0.297 moles) of 7-amino cephalosporanic acid (7-ACA) and 72.3 g (0.448 moles) of hexamethyl disilazane (HMDS) were taken in 600 ml of methylene chloride and were refluxed for 3-4 hrs. to give the silylated 7-amino cephalosporanic acid.

Step C: Preparation of 7-[4-bromo-2(Z)-methoxyimino-3-oxobutyramido]-cephalosporanic acid The solution of silylated 7-ACA in methylene chloride obtained from Step B was added to the solution of 4-bromo-2-methoxyimino-3-oxo butyric acid-N,N-dimethyl formiminium chloride chlorosulfate in methylene chloride obtained from Step A over a period of 30 mins, at a temperature maintained between −80 to −50° C. To the mixture was added 54 g (0.446 moles) of dimethylaniline and the progress of the reaction was monitored by HPLC and after completion of reaction gives the title compound i. e. 7-[4-bromo-2 (Z)-methoxyimino-3-oxobutyramido]-cephalosporanic acid.

$^1$H NMR (DMSO-d$_6$): δ, 9.43 (1H,d, NHCO), 5.80 (1H,dd, H-7), 5.14 (1H,d, H-6), 5.03, 4.61 (1H each, d, 3-CH$_2$OCOCH$_3$), 4.64 (2H,s, BrCH$_2$—), 4.06 (3H, s, —OCH$_3$), 3.64 (2H, ABq, SCH$_2$—), 2.02 (3H,s, OCOCH$_3$)

Step D: Preparation of Cefotaxime 27.2 g (0.3579 moles) of thiourea and 48.6 g (0.3573 moles) of sodium acetate tri hydrate was dissolved in 250 ml of water. This mixture was added to a mixture containing the solution of 7-[4-bromo-2(Z)-methoxyimino-3-oxobutyramido]-cephalosporanic acid in methylene chloride, as obtained in Step C and 490 ml of water over 30 mins. The reaction mixture was stirred for 2-3 hrs. The pH of the solution was adjusted to 5.5 with aqueous sodium bicarbonate.

The aqueous layer was separated and treated with activated carbon and filtered. To the filtrate 440 ml of tetrahydrofuran (THF) was added and the pH of the mixture was gradually adjusted to 2.8 with hydrochloric acid. The white solid obtained was filtered and dried at 45° C. for 4 hrs under vacuum to give 65.6 g (40.3% yield) of 7-[(Z)-2-(2-aminothiazol-4-yl)-2-methoxyiminoacetamido]cephalosporanic acid (cefotaxime)

Step E: Preparation of Cefotaxime Sodium 20 g (0.0438 moles) of cefotaxime (from Step D) was dissolved in a mixture of 40 ml methanol and 20 ml ethyl acetate using triethylamine. To the solution was added a solution of 8.4 g (0.0506 moles) of 2-ethyl sodium hexanoate, followed by 250 ml of ethyl acetate. The precipitated white solid was filtered and dried at 45° C. under vacuum to give 18.6 g (88.7% yield) of the sodium salt of 7-[(Z)-2-(2-aminothiazol-4-yl)-2-methoxyiminoacetamido]cephalosporanic acid (cefotaxime sodium) having a purity of 99.0%.

EXAMPLE-4

Preparation of disodium salt of 7-[(Z)-2-(2-amninothiazol-4-yl)-2-methoxyiminoacetamido]-3-[[2,5-dihydro-6-hydroxy-2-methyl-5-oxo-as-triazin-3-yl)thio]methyl]-3-cephem-4-carboxylic acid (ceftriaxone sodium)

Step A: Preparation of 4-bromo-2-methoxyimino-3-oxo butyric acid-N,N-dimethyl formiminium chloride chlorosulfate of formula (I)

The title compound was prepared as described in Example-2.

Step B: Preparation of silylated 7-amino-3-[[2,5-dihydro-6-hydroxy-2-methyl-5-oxo-as-triazin-3-yl)thio]methyl]-3-cephem-4-carboxylic acid 74.0 g (0.458 moles) of hexamethyldisilazane (HMDS) and 10.8 g (0.099 moles) of trimethyl chlorosilane (TMCS) was added to a suspension of the 100 g (0.2695 moles) of 7-amino-3-[[2,5-dihydro-6-hydroxy-2-methyl-5-oxo-as-triazin-3-yl)thio]methyl]-3-cephem-4-carboxylic acid and 800 ml of methylene chloride and the mixture refluxed was refluxed for 8 hrs to give silylated 7-amino-3-[[2,5-dihydro-6-hydroxy-2-methyl-5-oxo-as-triazin-3-yl)thio]methyl]-3-cephem-4-carboxylic acid.

Step C: Preparation of 7-[4-bromo-2(Z)-methoxyimino-3-oxobutyramido]-3-[[2,5-dihydro-6-hydroxy-2-methyl-5-oxo-as-triazin-3-yl)thio]methyl]-3-cephem-4-carboxylic acid (VIII)

The solution of silylated 7-amino-3-[[2,5-dihydro-6-hydroxy-2-methyl-5-oxo-as-triazin-3-yl)thio]methyl]-3-cephem-4-carboxylic acid in methylene chloride as obtained in Step B was added to the solution of 4-bromo-2-methoxyimino-3-oxo butyric acid-N,N-dimethyl formiminium chloride chlorosulfate in methylene chloride, as obtained from Step A over a period of 30 min while maintaining the temperature between −80 to −50° C. To the mixture was added 42.4 g. (0.350 moles) of dimethylaniline and the progress of the reaction was monitored by HPLC.

After completion of the reaction 800 ml of water and 400 ml of THF were added to the reaction mixture at room temperature and agitated. The organic layer containing 7-[4-bromo-2(Z)-methoxyimino-3-oxobutyramido]-3-[[2,5-dihydro-6-hydroxy-2-methyl-5-oxo-as-triazin-3-yl)thio]methyl]-3-cephem-4-carboxylic acid was separated and used as such for the next step.

Step D: Preparation of Ceftriaxone 24.6 g (0.323 moles) of thiourea and 22.6 g (0.269 moles) of sodium bi carbonate was dissolved in 200 ml of water. This mixture was added to a mixture containing the solution of 7-[4-bromo-2(Z)-methoxyimino-3-oxobutyramido]-3-[[2,5-dihydro-6-hydroxy-2-methyl-5-oxo-as-triazin-3-yl)thio]methyl]-3-cephem-4-carboxylic acid in the organic solvent, as obtained from Step C and 600 ml of water over a period of 30 mins. The reaction mixture was stirred for 60 mins at 5-10° C. The pH of the solution was adjusted to 5.5 with aqueous sodium bicarbonate solution. The reaction was further stirred for 2-3 hrs.

The aqueous layer was separated and treated with activated carbon and filtered. To the filtrate 360 ml of ethyl acetate and 78 ml of IPA were added and the pH of the mixture was gradually adjusted to 2.8 by addition of formic acid. The precipitated white solid of was filtered and dried at 45° C. for 4 hrs under vacuum to give 80.4 g (51.25% yield) of 7-[(Z)-2-(2-aminothiazol-4-yl)-2-methoxyiminoacetamido]-3-[[2,5-dihydro-6-hydroxy-2-methyl-5-oxo-as-triazin-3-yl)thio]methyl]-3-cephem-4-carboxylic acid (ceftriaxone) having a purity of 90.56%.

Step E: Preparation of Ceftriaxone Sodium 20 g (0.036 moles) of the ceftriaxone, obtained from from Step D was added to 120 ml water. To this was added triethylamine for complete dissolution of ceftriaxone. The clear solution was treated with activated carbon and filtered. To the filtrate was added 12.85 g (0.0774 moles) of 2-ethyl sodium hexanoate in 800 ml of acetone at 0-5° C. The precipitated white solid t was filtered, washed and dried under vacuum at 25° C. to give 18.5 g (77% yield) of the disodium salt of 7-[(Z)-2-(2-aminothiazol-4-yl)-2-methoxyiminoacetamido]-3-[[2,5-dihydro-6-hydroxy-2-methyl-5-oxo-as-triazin-3-yl)thio]methyl]-3-cephem-4-carboxylic acid (ceftriaxone sodium), having a purity of 94%.

EXAMPLE-5

Preparation of 7-[(Z)-2-(2-aminothiazol-4-yl)-2-methoxyiminoacetamido]-3-[[(2-furanylcarbonyl)thio]methyl]-3-cephem-4-carboxylic acid (ceftiofur)

Step A: Preparation of 4-bromo-2-methoxyimino-3-oxo butyric acid-N,N-dimethyl formiminium chloride chlorosulfate of formula (I)

The title compound was prepared as described in Example-2.

Step B: Preparation of silylated 7-amino-3-[[(2-furanylcarbonyl)thio]methyl]-3-cephem-4-carboxylic acid 30.4 g (0.1883 moles) of hexamethyldisilazane (HMDS) and 20.32 g (0.1873 moles) of trimethyl chlorosilane (TMCS) were added to the suspension of 80 g (0.2352 moles) of 7-amino-3-[[(2-furanylcarbonyl)thio]methyl]-3-cephem-4-carboxylic acid in 800 ml of methylene chloride and the mixture was refluxed for 3 hrs for complete silylation to give silylated 7-amino-3-[[(2-furanylcarbonyl)thio]methyl]-3-cephem-4-carboxylic acid.

Step C: Preparation of 7-[4-bromo-2(Z)-methoxyimino-3-oxobutyramido]-3-[[(2-furanylcarbonyl)thio]methyl]-3-cephem-4-carboxylic acid The solution of silylated 7-amino-3-[[(2-furanylcarbonyl)thio]methyl]-3-cephem-4-carboxylic acid in methylene chloride as obtained in Step B was added to the solution of 4-bromo-2-methoxyimino-3-oxo butyric acid-N,N-dimethyl formiminium chloride chlorosulfate in methylene chloride, as obtained from Step A over a period of 30 min while maintaining the temperature between −25 to −15° C. To the mixture was added 38.4 g. (0.173 moles) of dimethylaniline and the progress of the reaction was monitored by HPLC.

After completion of the reaction 800 ml of water was added to the reaction mixture at room temperature and agitated. The organic layer containing 7-[4-bromo-2(Z)-methoxyimino-3-oxobutyramido]-3-[[(2-furanylcarbonyl)thio]methyl]-3-cephem-4-carboxylic acid was separated and used as such for the next step.

$^1$HNMR (DMSO-$d_6$): δ, 5.93 (1H,dd, H-7), 5.17 (1H,d, H-6), 4.37 (1H,s,—S—CO—), 4.59 (2H,s, BrCH$_2$—), 4.20 (3H, s, —OCH$_3$), 3.78 (2H,s, SCH$_2$—).

IR (main bands) in cm$^{-1}$: 1780

Step D: Preparation of Ceftiofur 25.0 g (0.3289 moles) of thiourea was dissolved in 160 ml of demineralised water. This solution was added to a mixture containing 7-[4-bromo-2(Z)-methoxyimino-3-oxobutyramido]-3-[[(2-furanylcarbonyl)thio]methyl]-3-cephem-4-carboxylic acid in methylene chloride, as obtained from Step C 240 ml of tetrahydrofuran (THF) over a period of 30 mins. The reaction mixture was stirred for 2 hrs at 5-10° C. The pH of the solution was adjusted to 5.0 with aqueous sodium bicarbonate solution.

The aqueous layer was separated and the pH of the mixture was gradually adjusted to 3.0. The white solid precipitated was filtered and dried at 45° C. for 3 hrs under vacuum to give 1.65 g (21.4% yield) of 7-[(Z)-2-(2-aminothiazol-4-yl)-2-methoxyiminoacetamido)-3-[[(2-furanylcarbonyl)thio]methyl]-3-cephem-4-carboxylic acid (ceftiofur)

EXAMPLE-6

Following the methods described in Examples 1-5 the following cephalosporin compounds of formula (II) were prepared by utilizing the requisite starting compounds (I) and (VII). The compounds are:

i) 7-[(Z)-2-(2-aminothiazol-4-yl)-2-hydroxyiminoacetamido]-3-vinyl-3-cephem-4-carboxylic acid i.e. cefdinir,
ii) 7-((Z)-2-(2-amino-4-thiazolyl)-2-methoxyimino)acetyl]amino-3-[(Z)-2-(4methyl-5-thiazolyl)ethenyl-3-cephem-4-carboxylic acid, i.e. cefditoren and the pivaloyloxymethyl ester i. e. cefditoren pivoxil,
iii) 7-[(Z)-2-(2-aminothiazol-4-yl)-2-methoxyiminoacetamido]-3-(1-methylpyrrolodino)methyl-3-cephem-4-carboxylate i.e. cefepime,
iv) 7-[(Z)-2-(2-amiothiazol-4-yl)methoxyiminoacetamido]-3-methyl-3-cephem-4-carboxylic acid i.e. cefetamet, and the pivaloyloxymethyl ester i. e. cefetamet pivoxil,
v) 7-[(Z)-2-(2-aminothiazol]-4-yl)-2-carboxymethoxyiminoacetamido]-3-vinyl-3-cephem4-carboxylic acid i.e. cefixime,
vi) 7-[(Z)-2-(2-aminothiazol-4-yl)-2-methoxyiminoacetamido]-3-[[1-methyl-1H-tetrazol-5-yl]thio]methyl]-3-cephem-4-carboxylic acid i.e. cefmenoxime,
vii) 7-[(Z)-2-(2-aminothiazol-4-yl)-2-methoxyiminoacetamido]-3-[[[5-carboxymethyl)-4-methyl-2-thiazolyl]thio]methyl-3-3-cephem-4-carboxylic acid i.e. cefodizime,
viii) 7-[(Z)-2-(2-aminothiazol-4-yl)-2-methoxyiminoacetamido]-3-[[2,3-dihydro-2-(2-hydroxyethyl)-3-imino-1H-pyrazol-1-yl]methyl]-3-cephem-4-carboxylic acid i.e. cefoselis,
ix) 7-[(Z)-2-(2-aminothiazol-4-yl)-2-methoxyiminoacetamido]-3-[92,3-cyclopenteno-1-pyridinium)methyl]-3-cephem-4-carboxylic acid i.e. cefpirome,
x) 7-((Z)-2-(2-aminothiazol-4-yl)-2-methoxyiminoacetamido]-3-methoxymethyl-3-cephem-4-carboxylate—i.e. cefpodoxime and the 1-methylethoxycarbonyloxy ether i. e. cefpodoxime proxetil,
xi) 7-[(Z)-2-(2-aminothiazol-4-yl)-2-methoxyiminoacetamndo]-3-[[1-azabicyclo[4.2.0]oct-2-en-3-yl]methyl-5,6,7-tetrahydroquinolinium-4-carboxylic acid inner salt i. e. cefquinome,
xii) 7-[(Z)-2-(2-aminothiazol-4-yl)-2-(1-carboxy-1-methylethyl)oximinoacetamido}-3-[pyridinium]methyl-3-cephem-4-carboxylacid acid inner salt i. e. ceftazidime,
xiii) 7-[(Z)-2-(2-aminothiazol-4-yl)-2-methoxyiminoacetamido]-3-[2-(5-methyl-1,2,3,4-tetrazoyl)-methyl-3-cephem-4-carboxylic acid i. e. cefteram and the and the pivaloyloxymethyl ester i. e. cefteram pivoxil,
xiv) 7-[(Z)-2-(2-aminothiazol-4-yl)-2-methoxyiminoacetamido]-3-cephem-4-carboxylic acid i. e. ceftizoxime, and
xv) 7-[(Z)-2-(2-amninothiazol-4-yl)-2-methoxyiminoacetamido]-3-[(1,2,3-thiadiazol-5-ylthio)methyl]-3-cephem-4-carboxylic acid i. e. cefuzonam.

The invention claimed is:

1. A 4-halo-2-oxyimino-3-oxo butyric acid-N,N-dimethyl formiminium chloride chlorosulfate of formula (I) useful in the preparation of cephalosporin antibiotics

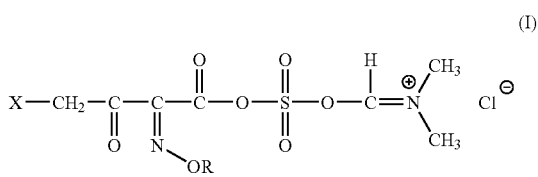

(I)

wherein X is chlorine or bromine;

R is hydrogen, $C_{1-4}$ alkyl group, a hydroxyl protective group selected from trialkyl silyl ethers; trialkyl aryl silyl ethers; trialkyl stannyl ethers; trityl; tetrahydropyranyl; alkyl or aryl sulphonates selected from tosyl, mesyl, and besyl; boron or aluminum containig two alkyl groups; unsubstituted benzyl; or —CH$_2$COOR$_5$, or —C(CH$_3$)$_2$COOR$_5$;

wherein R$_5$ is hydrogen; or a hydrolysable ester group selected from lower alkyl esters; alkanoyloxy alkyl esters selected from acetoxy methyl, pivaloxy methyl, 1-acetoxy ethyl, and 1-pivaloxyethyl; lower alkoxycarbonyloxyalkyl esters; alkoxymethyl esters; lower alkyl amino methyl; benzyl ester; and cyanomethyl ester.

2. A process for preparation of compound of formula (I)

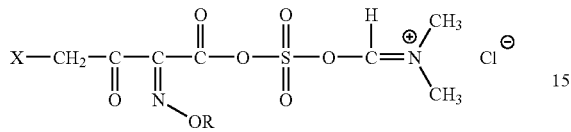

comprising reacting 4-halo-2-oxyimino-3-oxobutyric acid of formula (IV$^1$),

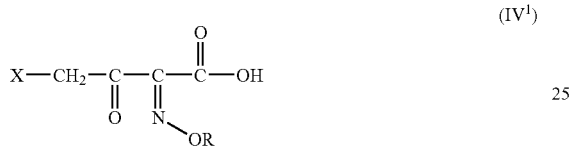

wherein X is chlorine or bromine;

R is hydrogen, C$_{1-4}$ alkyl group, a hydroxyl protective group selected from trialkyl silyl ethers; trialkyl aryl silyl ethers; trialkyl stannyl ethers; trityl; tetrahydropyranyl; alkyl or aryl sulphonates selected from tosyl, mesyl, and besyl; boron or aluminum containig two alkyl groups; unsubstituted benzyl; or —CH$_2$COOR$_5$, or —C(CH$_3$)$_2$COOR$_5$;

wherein R$_5$ is hydrogen; or a hydrolysable ester group selected from lower alkyl esters; alkanoyloxy alkyl esters selected from acetoxy methyl, pivaloxy methyl, 1-acetoxy ethyl, and 1-pivaloxyethyl; lower alkoxycarbonyloxyalkyl esters; alkoxymethyl esters; lower alkyl amino methyl; benzyl ester; and cyanomethyl ester with N,N-dimethylformiminium chloride chlorosulphate of formula (VII)

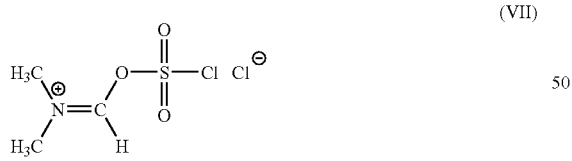

in an organic solvent at a temperature ranging from –30° C. to –15° C.

3. The process according to claim 2, wherein the organic solvent is chlorinated solvents selected from dichloromethane, dichloroethane, and chloroform; aromatic hydrocarbons selected from benzene and toluene; and nitriles selected from acetonitrile, propionitrile and butyronitrile.

4. The process according to claim 2, wherein the molar ratio of compound of formula (VII) to compound of formula (IV$^1$) is between 1.1 to 1.3.

5. A process for preparation of a cephalosporin compound of formula (II),

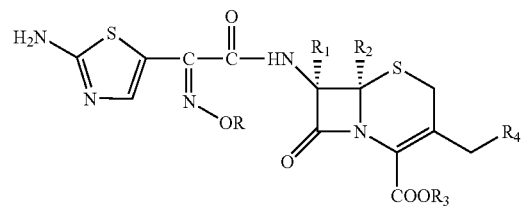

wherein

R is hydrogen, C$_{1-4}$ alkyl group, a hydroxyl protective group selected from trialkyl silyl ethers; trialkyl aryl silyl ethers; trialkyl stannyl ethers; trityl; tetrahydropyranyl; alkyl or aryl sulphonates selected from tosyl, mesyl, and besyl; boron or aluminum containing two alkyl groups; unsubstituted benzyl; or —CH$_2$COOR$_5$, or —C(CH$_3$)$_2$COOR$_5$;

wherein R$_5$ is hydrogen; or a hydrolysable ester group selected from lower alkyl esters; alkanoyloxy alkyl esters selected from acetoxy methyl, pivaloxy methyl, 1-acetoxy ethyl, and 1-pivaloxyethyl; lower alkoxycarbonyloxyalkyl esters; alkoxymethyl esters; lower alkyl amino methyl; benzyl ester; and cyanomethyl ester, R$_1$ is hydrogen or OCH$_3$;

R$_2$ is hydrogen;

R$_3$ is hydrogen, a negative charge or ester selected from the group of lower alkyl esters; alkanoyloxy alkyl esters selected from acetoxy methyl, pivaloxymethyl, 1-acetoxyethyl, and 1-pivaloxyetyl ester; lower alkoxy carbonyloxyalkyl esters selected from methoxycarbonyloxymethyl, 1-ethoxycarbonyloxyethyl and 1-isopropoxycarbonyloxy-ethyl ester; alkoxy methyl esters; lower alkyl aminomethyl esters; acetamidomethyl ester; benzyl ester; and cyanomethyl ester, R$_4$ is hydrogen or is a substituent selected from unsubstituted and substituted alkyl; and unsubstituted and substituted alkenyl; wherein substituted alkyl andlpr alkenvi beinzsubstituted by alkoxy, heterocyclicthio, heterocycyliccarbonylthio, alkylcarbonyloxy or heterocyclyl;

comprising reaction of compound of formula (I)

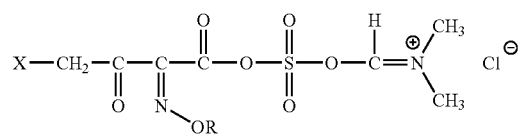

wherein X is chlorine or bromine; R and R$_5$ are selected from corresponding groups listed for those of formula (II) above with 7-amino cephalosporanic acid of formula (V),

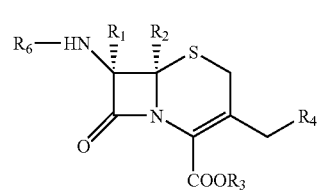

wherein R₁ and R₂ are selected from corresponding groups listed for those of formula (II) above; R₃ is selected from a group listed for R₃ of formula (II) above or a trialkyl silyl group; R₄ is selected from a group listed for R₄ of formula (II) above; R₆ is hydrogen or a trialkyl sily group with the proviso that, when R₃ is hydrogen, R₆ is also hydrogen; when R₃ is a trialkyl silyl group, R₆ is also a trialkyl silyl group; and when R₃ is an ester, R₆ is hydrogen to give 7-[-(4-halo-2-oxyimino-3-oxobutyramido)-3-substituted-3-cephem-4-carboxylic acid of formula (VIII),

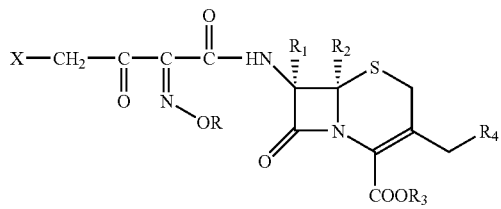

(VIII)

wherein X, R, R₁, R₂, R₃ and R₄ are corresponding groups listed for those of formula (I) or (II) above followed by cyclisation of compound (VIII) with thiourea.

6. The process according to claim 5, wherein the reaction of compound (I) and compound (V) to give compound (VIII) is carried out in an organic solvent and in the presence of a base at a temperature ranging from −80° C. to −15° C.

7. The process according to claim 6, wherein the organic solvent is selected from chlorinated solvents; aromatic hydrocarbons; nitrile solvents; and ethers.

8. The process according to claim 6, wherein the base is selected from N,N dimethyl aniline, diethyl amine, and pyridine.

9. The process according to claim 5, wherein the molar ratio of compound (I) to the cephalosporin compound (V) is between 1.1 to 2.0.

10. The process according to claim 5, wherein the preferred temperature is between −55° C. to −25° C.

11. The process according to claim 5, wherein the reaction of compound (VIII) and thiourea to give the cephalosporin compounds of formula (II) is carried out in a mixture of organic solvent and water and in the presence of a base at low to ambient temperature.

12. The process according to claim 11, wherein the organic solvent is selected from chlorinated solvents; aromatic hydrocarbons; nitrile solvents; and ethers.

13. The process according to claim 6, wherein the base is selected from alkali metal carbonates, such as sodium carbonate, potassium carbonate and lithium carbonate; alkali metal hydrogen carbonates, such as sodium hydrogen carbonate and potassium carbonate; and alkali metal acetates, such as sodium acetate and potassium acetate.

14. The process according to claim 5, wherein a temperature at which the reaction is carried out is between −5° C. and 40° C.

15. A process according to claim 5, wherein the compound of formula (II) is any one of
   i) 7-[(Z)-2-(2-aminothiazol-4-yl)-2-hydroxyiminoacetamido]-3-vinyl-3-cephem-4-carboxylic acid i.e. cefdinir,
   ii) 7-[(Z)-2-(2-amino-4-thiazolyl)-2-methoxyimino)acetyl]amino-3-[(1Z)-2-(4-methyl-5-thiazolyl)ethenyl-3-cephem-4-carboxylic acid, i.e. cefditoren and the pivaloyloxymethyl ester i. e. cefditoren pivoxil,
   iii) 7-[(Z)-2-(2-aminothiazol-4-yl)-2-methoxyiminoacetamido]-3-(1-methylpyrrrolodino)methyl-3-cephem-4-carboxylate i.e. cefepime,
   iv) 7-[(Z)-2-(2-aminothiazol-4-yl)methoxyiminoacetamido]-3-methyl-3-cephem-4-carboxylic acid i.e. cefetamet, and the pivaloyloxymethyl ester i. e. cefetamet pivoxil,
   v) 7-[(Z)-2-(2-aminothiazol-4-yl)-2-carboxymethoxyiminoacetamido]-3-vinyl-3-cephem-4-carboxylic acid i.e. cefixime,
   vi) 7-[(Z)-2-(2-aminothiazol-4-yl)-2-methoxyiminoacetamido]-3-[[1-methyl-1H-tetrazol-5-yl]thio]methyl]-3-cephem-4-carboxylic acid i.e. cefmenoxime,
   vii) 7-[(Z)-2-(2-aminothiazol-4-yl)-2-methoxyiminoacetamido]-3-[[[5-carboxymethyl)-4-methyl-2-thiazolyl]thio]methyl]-3-cephem-4-carboxylic acid i.e. cefodizime,
   viii) 7-[(Z)-2-(2-aminothiazol-4-yl)-2-methoxyiminoacetamido]-3-[[2,3-dihydro-2-(2-hydroxyethyl)-3-imino-1H-pyrazol-1-yl]methyl]-3-cephem-4-carboxylic acid i.e. cefoselis,
   ix) 7-[(Z)-2-(2-aminothiazol-4-yl)-2-methoxyiminoacetamido]cephalosporanic acid i.e. cefotaxime,
   x) 7-[(Z)-2-(2-aminothiazol-4-yl)-2-methoxyiminoacetamido]-3-[92,3-cyclopenteno-1-pyridinium)methyl]-3-cephem-4-carboxylic acid i.e. cefpirome,
   xi) 7-[(Z)-2-(2-aminothiazol-4-yl)-2-methoxyiminoacetamido]-3-methoxymethyl-3-cephem-4-carboxylate— i.e. cefpodoxime and the 1-methylethoxycarbonyloxy ether i. e. cefpodoxime proxetil,
   xii) 7-[(Z)-2-(2-aminothiazol-4-yl)-2-methoxyiminoacetamido]-3-[[1-azabicyclo[4.2.0]oct-2-en-3-yl]methyl-5,6,7-tetrahydroquinolinium-4-carboxylic acid inner salt i. e. cefquinome,
   xiii) 7-[(Z)-2-(2-aminothiazol-4-yl)-2-(1-carboxy-1-methylethyl)oximinoacetamido}-3-[pyridinium]methyl-3-cephem-4-carboxylacid acid inner salt i. e. ceftazidime,
   xiv) 7-[(Z)-2-(2-aminothiazol-4-yl)-2-methoxyiminoacetamido]-3-[2-(5-methyl-1,2,3,4-tetrazoyl)-methyl-3-cephem-4-carboxylic acid i. e. cefteram and the and the pivaloyloxymethyl ester i. e. cefteram pivoxil,
   xv) 7-[(Z)-2-(2-aminothiazol-4-yl)-2-methoxyiminoacetamido]-3-[[(2-furanylcarbonyl)thio]methyl]-3-cephem-4-carboxylic acid i. e. ceftiofur,
   xvi) 7-[(Z)-2-(2-aminothiazol-4-yl)-2-methoxyiminoacetamido]-3-cephem-4-carboxylic acid i. e. ceftizoxime,
   xvii) 7-[(Z)-2-(2-aminothiazol-4-yl)-2-methoxyiminoacetamido]-3-[[2,5-dihydro-6-hydroxy-2-methyl-5-oxo-as-triazin-3-yl)thio]methyl]-3-cephem-4-carboxylic acid i. e. ceftriaxone, and
   xviii) 7-[(Z)-2-(2-aminothiazol-4-yl)-2-methoxyiminoacetamido]-3-[(1,2,3-thiadiazol-5-ylthio)methyl]-3-cephem-4-carboxylic acid i. e. cefuzonam.

16. The compound of formula (I) according to claim 1, wherein R₅ is lower alkyl ester selected from methyl, ethyl, and tertiary butyl; lower alkoxycarbonyloxyalkyl ester selected from methoxycarbonyloxymethyl, 1-ethoxycarbonyloxyethyl, and 1-isopropoxycarbonyloxy ethyl; methoxymethyl ester; or acetamidomethyl ester.

17. The process according to claim 2, wherein R₅ is lower alkyl ester selected from methyl, ethyl, and tertiary butyl; lower alkoxycarbonyloxyalkyl ester selected from methoxycarbonyloxymethyl, 1-ethoxycarbonyloxyethyl, and 1-isopropoxycarbonyloxy ethyl; methoxymethyl ester; and acetamidomethyl ester.

18. The process according to claim 5, wherein $R_5$ is lower alkyl ester selected from methyl, ethyl, and tertiary butyl; lower alkoxycarbonyloxyalkyl ester selected from methoxycarbonyloxymethyl, 1-ethoxycarbonyloxyethyl, and 1-isopropoxycarbonyloxy ethyl; methoxymethyl ester; and acetamidomethyl ester.

19. The process according to claim 5, wherein $R_3$ is lower alkyl ester selected from methyl, ethyl and tertiary butyl; and methoxymethyl ester.

20. The process according to claim 6, wherein the organic solvent is chlorinated solvent selected from dichioromethane, diebioroethane, and chloroform; aromatic hydrocarbon selected from benzene and toluene; nitrile solvent selected from acetonitrile, propionitrile, and butyronitrile; or ethers selected from tetrahydrofuran and dioxane.

21. The process according to claim 11, wherein the organic solvent is chlorinated solvent selected from dichioromethane, dichloroethane, and chloroform; aromatic hydrocarbon selected from benzene and toluene; nitrile solvent selected from acetonitrile, propionitrile, and butyronitrile; or ethers selected from tetrahydrofuran and dioxane.

* * * * *